United States Patent
Highsmith (10) Patent No.: US 9,878,131 B2
(45) Date of Patent: Jan. 30, 2018

(54) GUIDE WIRE RESTRAINT DEVICE

(71) Applicant: BIOSENSE WEBSTER (ISRAEL) LTD., Yokneam (IL)

(72) Inventor: Debby Esther Highsmith, Laguna Niguel, CA (US)

(73) Assignee: Biosense Webster (Israel) Ltd., Yokneam, IL (US)

( * ) Notice: Subject to any disclaimer, the term of this patent is extended or adjusted under 35 U.S.C. 154(b) by 256 days.

(21) Appl. No.: 14/566,649

(22) Filed: Dec. 10, 2014

(65) Prior Publication Data
US 2016/0166808 A1    Jun. 16, 2016

(51) Int. Cl.
  *A61M 25/09*    (2006.01)
  *A61B 17/00*    (2006.01)
  *A61M 25/01*    (2006.01)

(52) U.S. Cl.
  CPC ...... *A61M 25/09* (2013.01); *A61M 25/09041* (2013.01); *A61B 2017/00469* (2013.01);
  (Continued)

(58) Field of Classification Search
  CPC ............ A61M 25/09; A61M 25/09041; A61M 25/0169; A61M 2025/09125; A61M 2025/09116; A61B 2017/00469
  (Continued)

(56) References Cited

U.S. PATENT DOCUMENTS 1,919,953 A * 7/1933 Knutson ............ H01R 4/4872
                                                439/817

2,820,563 A * 1/1958 Bronnimann .......... B65D 41/16
                                                215/253
(Continued)

FOREIGN PATENT DOCUMENTS

EP           0 801 955 A1    10/1997
WO    WO 2007/124076 A1    11/2007
WO    WO 2008/013441 A1     1/2008

OTHER PUBLICATIONS

European Search Report dated Sep. 23, 2016 for EP Application No. 15198737.7, 13 pages.
(Continued)

*Primary Examiner* — David J McCrosky
(74) *Attorney, Agent, or Firm* — Lewis Roca Rothgerber Christie LLP (57) ABSTRACT

A device for restraining a guide wire includes a base having a recessed formation configured to receive a portion of the guide wire, and a flexible lid configured to fit on the base. The lid has a main sheet portion covering the portion of the guide wire and a plurality of fingers separated by gaps and extending downwardly from a peripheral edge of the main sheet portion to surround the base. Sandwiched between the lid and base, the guide wire extends through gaps between the finger members. Constructed of sheet material, the lid is flexibly movable between a closed configuration wherein the fingers are flexed inwardly engaging the base, and an open configuration wherein the fingers are flexed outwardly releasing the base. Alternatively, a clamping device for restraining a guide wire includes top and bottom clamp members and a pivot connection, wherein the top clamp member has a handle end and a securing end and wherein the pivot connection enables the top clamp member to pivot between a closed position restraining the guide wire and an open position releasing the guide wire.

15 Claims, 7 Drawing Sheets

(52) U.S. Cl.
CPC .................. *A61M 25/0169* (2013.01); *A61M 2025/09116* (2013.01); *A61M 2025/09125* (2013.01)

(58) Field of Classification Search
USPC .......................... 220/322, 323; 215/271, 272
See application file for complete search history.

(56) References Cited

U.S. PATENT DOCUMENTS

| | | | | |
|---|---|---|---|---|
| 2,985,329 | A * | 5/1961 | Jente | B65D 41/18 215/301 |
| 3,016,510 | A * | 1/1962 | Blonder | H01R 4/2479 439/411 |
| 3,312,128 | A | 4/1967 | Wasson | |
| 3,509,517 | A * | 4/1970 | Gutshall | H01R 4/2479 439/411 |
| 4,653,501 | A * | 3/1987 | Cartmell | A61B 5/04087 600/392 |
| 4,907,332 | A * | 3/1990 | Christian | A61M 25/09 600/434 |
| 5,325,868 | A | 7/1994 | Kimmelstiel | |
| 6,030,349 | A | 2/2000 | Wilson et al. | |
| 6,371,940 | B1 * | 4/2002 | Valencia | A61M 25/0169 600/585 |
| 7,011,635 | B1 | 3/2006 | Delay | |
| 8,277,417 | B2 | 10/2012 | Fedinec | |
| 8,523,824 | B2 | 9/2013 | Teirstein et al. | |
| 9,127,786 | B1 | 9/2015 | Arratia | |
| 2007/0016105 | A1 | 1/2007 | Mamourian | |
| 2010/0147900 | A1 * | 6/2010 | Tardif | A47G 19/24 222/498 |
| 2011/0178506 | A1 | 7/2011 | Numata et al. | |
| 2012/0216385 | A1 | 8/2012 | Taylor | |
| 2013/0131593 | A1 * | 5/2013 | Selkee | A61M 25/0136 604/95.04 |

OTHER PUBLICATIONS

European Search Report for EP Patent Application No. 15198737.7, dated May 17, 2016, 7 pages.

* cited by examiner

GUIDE WIRE RESTRAINT DEVICE

FIELD OF INVENTION

This invention relates to guide wire accessories, in particular, devices for holding and restraining guide wires.

BACKGROUND

A guide wire typically includes an elongated wire body, a protective coating layer covering a distal portion of the wire body, and an annular member disposed on a proximal portion of the resin coating layer. As its name suggests, a guide wire is a wire or elongated member that "guides" a catheter or endoscope through a desired vessel of a patient's body. The guide wire itself may be introduced into the vessel through a trocar which is withdrawn. When the guide wire has been advanced to the region of interest in the patient's body, the catheter or endoscope is passed over the guide wire to reach the region of interest.

In advancing the guide wire to the region of interest, the physician often has to rotate and deflect the guide wire. Such rotation and deflection may cause torsional energy to be stored in the body of the guide wire which may dislodge the guide wire if the guide wire is released by the physician. Thus, the physician or an assistant must hold the exposed portion of the guide wire at least while the catheter or endoscope is passed over the guide wire, if not also during a procedure such as renal denervation or coronary or peripheral intervention when a guide wire is used in conjunction with a catheter. To use an assistant simply for holding the guide wire is not desirable for multiple reasons, including but not limited to the following: increase cost of procedure, decrease workspace in operating room, and increase communication dependency between physician and assistant.

Accordingly, there is a desire for a device that can releasably restrain a guide wire under a one-handed operation by a user. There is a further desire to for the device to be relatively small and portable, and to sit stably in position on the patient's body or on the patient table.

SUMMARY OF THE INVENTION

The present invention is directed to a device for restraining a guide wire by securing a portion of the guide wire between top and bottom members, wherein the top member is configured to readily flex between an open configuration and a closed configuration allowing for single-handed, ergonomic operation by a user. In one embodiment, the device includes a base member having a recessed formation configured to receive a portion of the guide wire, and a flexible lid member configured to fit on the base member, with the portion of the guide wire extending between the lid and base members. The lid member has a main sheet portion covering the portion of the guide wire and a plurality of finger members that extend downwardly from the main sheet portion to generally surround an upper portion of the base, with the portion of the guide wire extends through a first gap and a second gap between the finger members. Advantageously, the lid member is flexibly movable between a closed configuration wherein the finger members are flexed inwardly to engage the base member and clamp on the guide wire, and an open configuration wherein the finger members are flexed outwardly to release the base member and the guide wire.

In a more detailed embodiment, the main sheet portion flexes between a convex shape and a concave shape, wherein the convex shape holds the finger members inwardly and the concave shape flexes the finger members outwardly.

In a more detailed embodiment, the base member has a circumferential groove which receives distal ends of the finger members when the lid member is in the closed position. The distal ends of the finger members trace a larger circumference when the lid member is in an open configuration and a smaller circumference when the lid member is in a closed configuration. The circumference traced by the distal ends of the finger members when the lid member is in a closed configuration is equal or less than a circumference of the circumferential groove. The circumference traced by the distal ends of the finger members when the lid member is in an open configuration is greater than the circumference of the circumferential groove.

In a more detailed embodiment, each finger member of the lid is bent inwardly at a junction between an upper portion and a lower portion of each finger member, wherein the junctions and distal ends of the finger members trace respectively larger circumferences when the lid member is in the open configuration, and the junctions and distal ends of the finger members trace respectively smaller circumferences by the junctions and the distal ends when the lid member is in the closed configuration. The junction provides the lid with an ergonomic profile that facilitates one-handed operation by the user.

In a more detailed embodiment, each of the first and second gaps through which the portion of the guide wire extends is lined with a friction-inducing material for gripping and preventing damage and/or permanent deformation to the guide wire. When the lid and base members are in the closed or secured configuration, the first and second gaps between the finger members through which the guide wire extends are each smaller than an outer diameter of the guide wire wherein the friction-inducing material lining the gaps is compressible by the guide wire.

The present invention is also directed to clamping device for restraining a guide wire. In one embodiment, clamping device comprises top and bottom clamp members and a pivot connection, wherein the top clamp member has a handle end and a securing end, the handle end being configured for a user to depress toward the bottom clamp member, the securing end being configured to press and grip a portion of the guide wire against the bottom clamp member, and wherein the pivot connection enables the top clamp member to pivot between a closed position restraining the guide wire and an open position releasing the guide wire.

In a detailed embodiment, the device includes a bias member configured to bias the top member into the closed position. The securing end of the top member includes a friction-inducing material for contact with the portion of the guide wire when the top member is in a closed position.

In a more detailed embodiment, the pivot connection includes a pin and the bias member includes a leaf spring.

The present invention provides devices that are simple in design, have low construction cost, and can be disposable or resterilizable. The devices eliminate the need for assistance in holding the guide wire and provides a clutter-free workspace.

BRIEF DESCRIPTION OF THE DRAWINGS

These and other features and advantages of the present invention will be better understood by reference to the following detailed description when considered in conjunction with the accompanying drawings wherein.

DETAILED DESCRIPTION OF THE INVENTION

Figure 1:
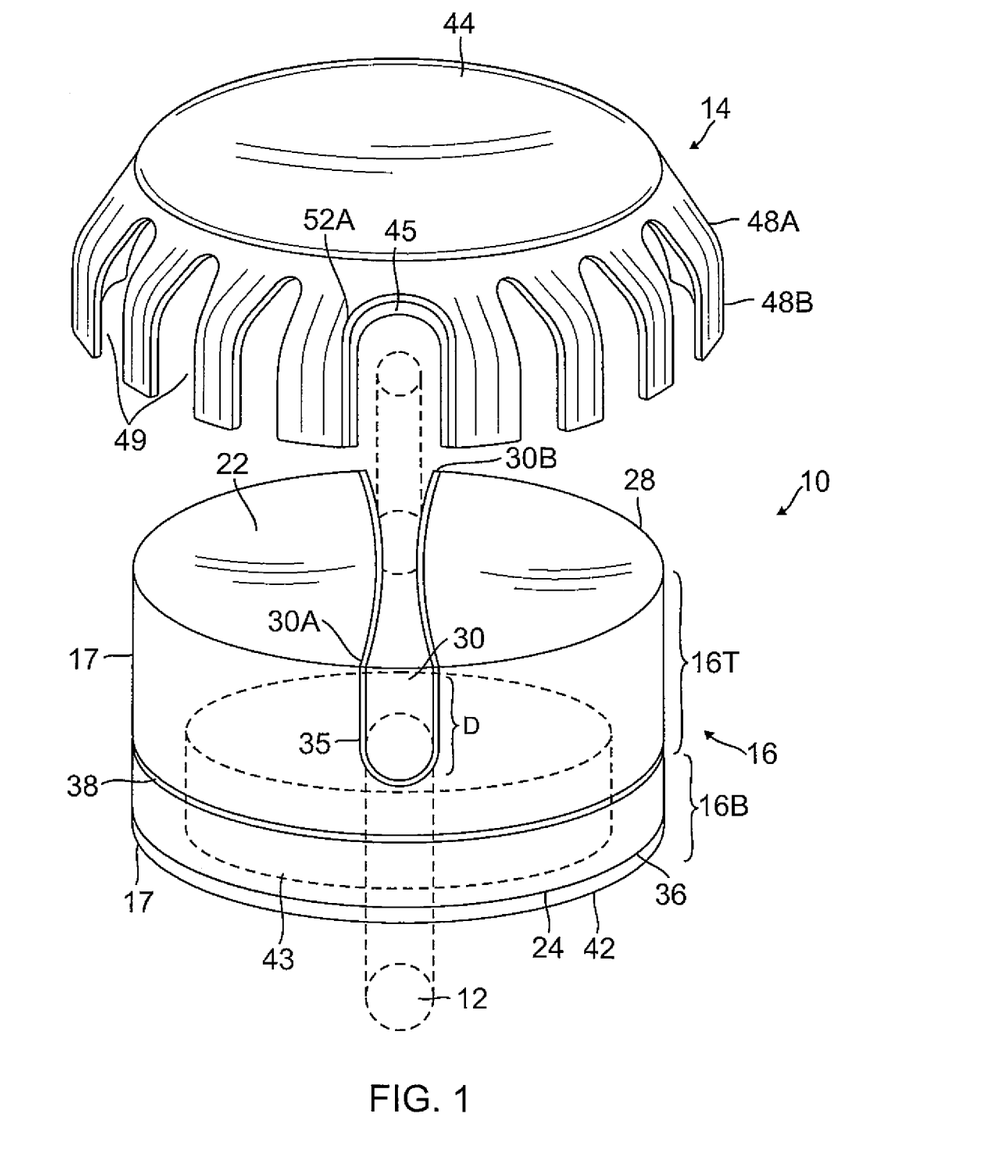
FIG. 1 is an exploded perspective view of a device of the present invention, according to one embodiment.

With reference to FIG. 1, the present invention is directed a restraint device 10 to releasably secure a tensile member 12, e.g., a guide wire, in a selected position and/or orientation preventing rotation or translation of the tensile member. The restraint device has an upper member or lid 14 and a lower member or base 16 adapted for releasable engagement between an engaged or closed position (FIG. 2A) and a release or open position (FIG. 2B) with each other for releasably securing the tensile member 12 therebetween.

In one or more embodiments, the device 10 when assembled has an overall configuration resembling a "hockey puck" or disc with a circular cross-section. Depending on the size of the tensile member 12 restrained by the device 10, the disc may have a diameter ranging between about 3.0 inches and 5.0 inches, and preferably about 4.0 inches, and a thickness of about 0.5 inch and 1.5 inches, and preferably about 1.0 inches. However, it is understood that the device may have any cross-sectional shape, for example, polygonal (including rectangular, triangular), oval, etc.

Figure 3A:
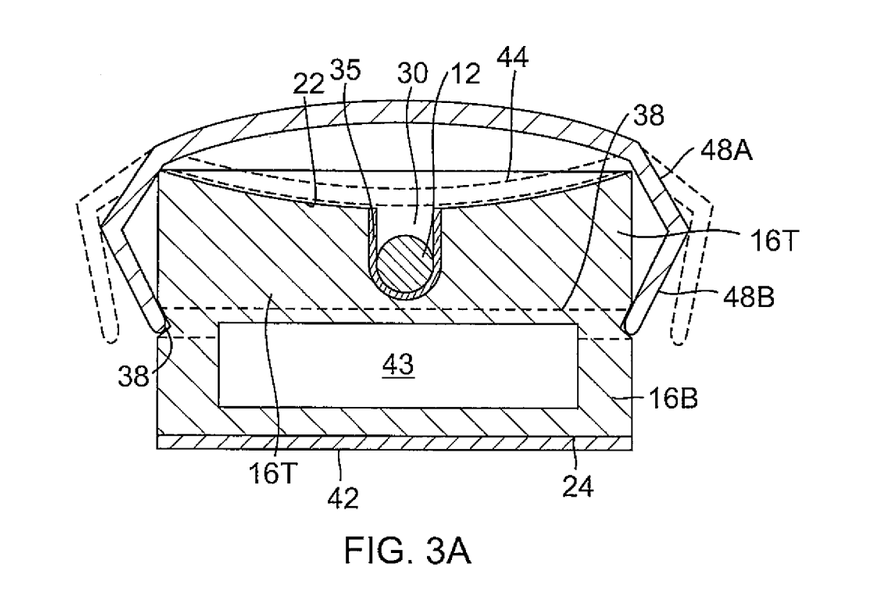
FIG. 3A is a side cross-sectional view of the device, illustrating the closed configuration in solid lines and the open configuration in broken lines

As shown in FIGS. 1 and 3A, the base 16 has a top surface 22, a bottom surface 24, having generally vertically linear side profile 17 and a circumferential groove 38 that extends laterally around the base 16 which visually divides the base into a top base portion 16T and a bottom base portion 16B. The top base portion 16T and the bottom base portion 16B have generally similar widths although the top base portion 16T may have a greater thickness in the vertical direction than the bottom base portion 16B. It is understood that "peripheral edge" and "circumference" are used interchangeably herein and that "circumference" or "circumferential" are used loosely without limiting the shape of the underlying object or structure to a circular or round shape, in that the latter may have any cross-sectional shape, e.g., rectangular, triangular, oval, etc. The top surface 22 surrounded by the circumferential edge 28 is, for example, circular, and has a concave shape. The top surface 22 has a recessed formation or channel 30 with a cross-sectional shape configured to receive at least a portion of the tensile member 12. In one or more embodiments, the tensile member 12 has a circular cross-section, and the recessed formation 30 has a depth D that is greater than the diameter of the guide wire, wherein a bottom of the depth has a hemispherical cross-sectional shape corresponding to the circular cross-section of the guide wire. The recessed formation 30 extends linearly across the top surface 22, e.g., diametrically across the top surface 22, such that the recessed formation has a first end 30A and a second end 30B at the top circumferential edge 28. The recessed formation 30 is lined with a compressible friction-inducing padding material or coating 35 on which the tensile member 12 may lie.

A bottom surface 24 of the base 16 is generally planar with a bottom surface area that is circumscribed by a bottom peripheral edge or circumferential edge 36 that is at least generally equal to or greater than the top circumferential edge 28.

The base 16 may have a solid body with a mass that weighs down the device for stability. In that regard the base 16 may be constructed of one or more weighty materials, for example, metal and/or plastic, and/or at least the bottom portion 16U may have an inner cavity 43 (shown in FIGS. 1 and 3A) that can be filled with a weighty filler material, for example, sand or a fluid, to provide the device 10 with sufficient weight and a lower center of gravity to remain stationary on a support surface or patient's body while holding the tensile member 12. At least a portion of the bottom surface 24, if not the surface in its entirety, is covered by a layer 42 of friction-inducing material or an adhesive to provide the device 10 with traction on the support surface. Other fasteners that may be applied to the device and/or the bottom surface 24 include, for example, suction cup(s), magnets, screws, ties, or the like.

Figure 4A:
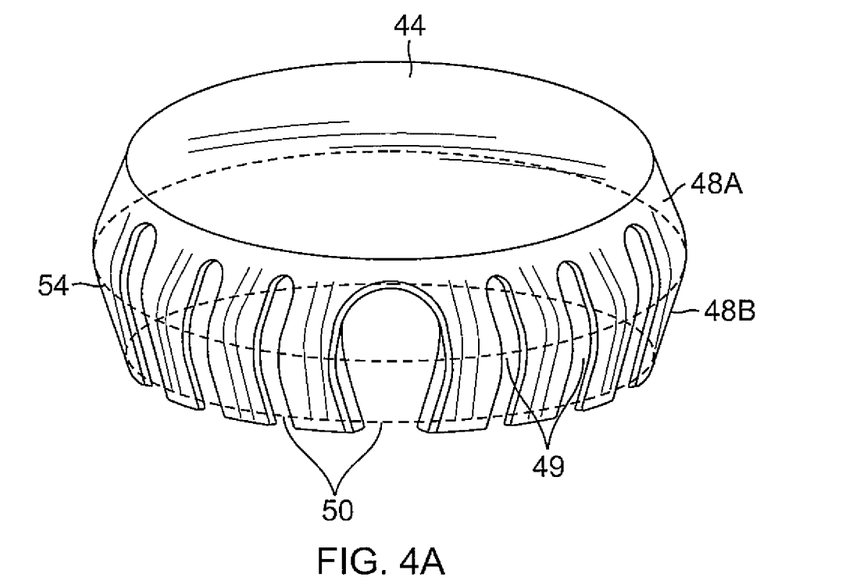
FIG. 4A is a perspective view of an upright lid member of the device of FIG. 1.
Figure 4B:
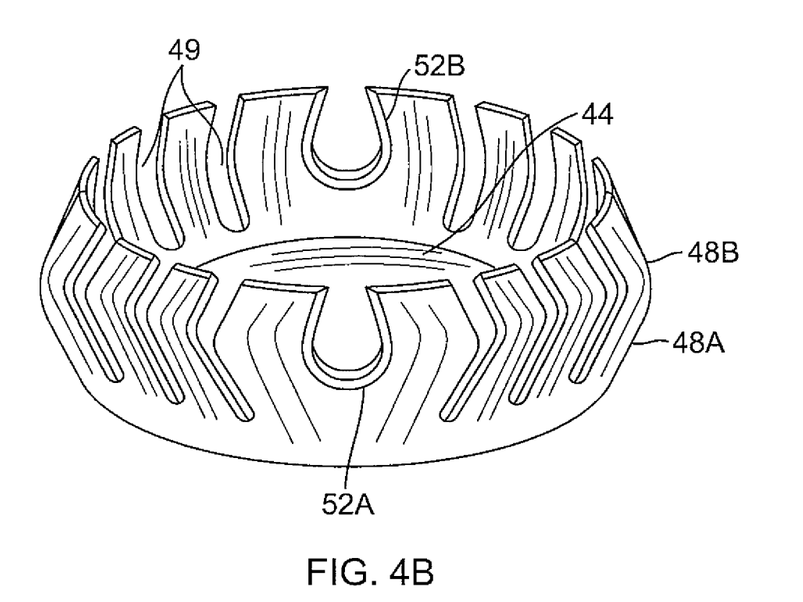
FIG. 4B is a perspective view of an upside down lid member of the device of FIG. 1

With reference to FIGS. 4A and 4B, the lid 14 has a main sheet portion 44 defined by a first circumferential edge 46 and a plurality of elongated finger members 48, separated by space gaps 49 between adjacent finger members, that extend downwardly from the peripheral edge 46. The main sheet portion 44 is configured and sized to cover the top surface 22 of the base 16. In the illustrated embodiment, the main sheet portion 44 is circular to match the circular shape of the base top surface 22. The plurality of finger members may be as many as desirable or appropriate. In one embodiment, the plurality ranges between about 10 and 20, preferably between about 12 and 18, and more preferably about 16. The finger members 48 form a "skirt" that is adapted to generally surround the top base portion 16T down to the circumferential groove 38 when the lid 14 is placed on the base 16. Each finger member 48 is bent to define a junction between a first and upper finger section 48A, and a second and lower finger section 48B.

The lid 14 may be made of any suitable resilient material that provides sufficient rigidity with sufficient elastic flexibility, for example, sheet metal or sheet plastic. In one or more embodiments, the lid 14 is formed by stamping a planar sheet of suitable material and generally uniform thickness to provide the shape of the main sheet portion 44 with the radially extending finger members 48, wherein the stamping also permanently deforms the main sheet portion 44 and the finger members 48 with desired shape and angles. In one embodiment, the stamping permanently deforms the main sheet portion 44 with a convex shape with the finger members 48 bent at a smaller angles θ1 and θ2, where the angle θ1 is defined by the upper finger section 48A from the vertical side profile 17 of the top base portion 16T and the angle θ2 is defined between the lower finger section 48B and the upper finger section 48A. So stamped, the lid 14 assumes this configuration in its relaxed or neutral state in which the distal ends of the finger members 48 trace a circumference 50 (see broken lines FIG. 4A) that is equal to or slightly less than the circumferential waist 38 of the base 16, and the angle θ1 ranges between about 45 and 65, and preferably about 55, and the angle θ2 ranges between about 135 and 160, and preferably about 145. The relaxed or neutral state of the lid 14 also entail the junctions between the upper and lower finger sections 48A and 48B tracing a circumference 54 (see FIG. 4A) that is greater than the circumference the top base portion 16T (see FIG. 1). As such, when the lid 14 engages the base 16 in the closed position (FIG. 2A), distal ends of the finger members 48 are received in the circumferential waist 38 to releasably secure the lid 14 on the base 16.

Accordingly, when the lid 14 is in the closed configuration, the upper finger section 48A is bent at angle θ1 from the vertical, and the lower finger section 48B is bent at angle θ2 from the upper finger section 48A (see FIG. 3A). The angles θ1 and θ2 enable the finger members 48 to curl around the upper base portion 16T and grip it via the circumferential groove 38. In that regard, each finger member 48 has a length that allows it to reach the "waist" or circumferential groove 38 of the base 16 such that a distal edge of the each finger 48 can be received and sit in the groove 38. In the illustrated embodiment, the groove 38 has a notched or "V" shaped cross section (see FIG. 3B).

Figure 2A:
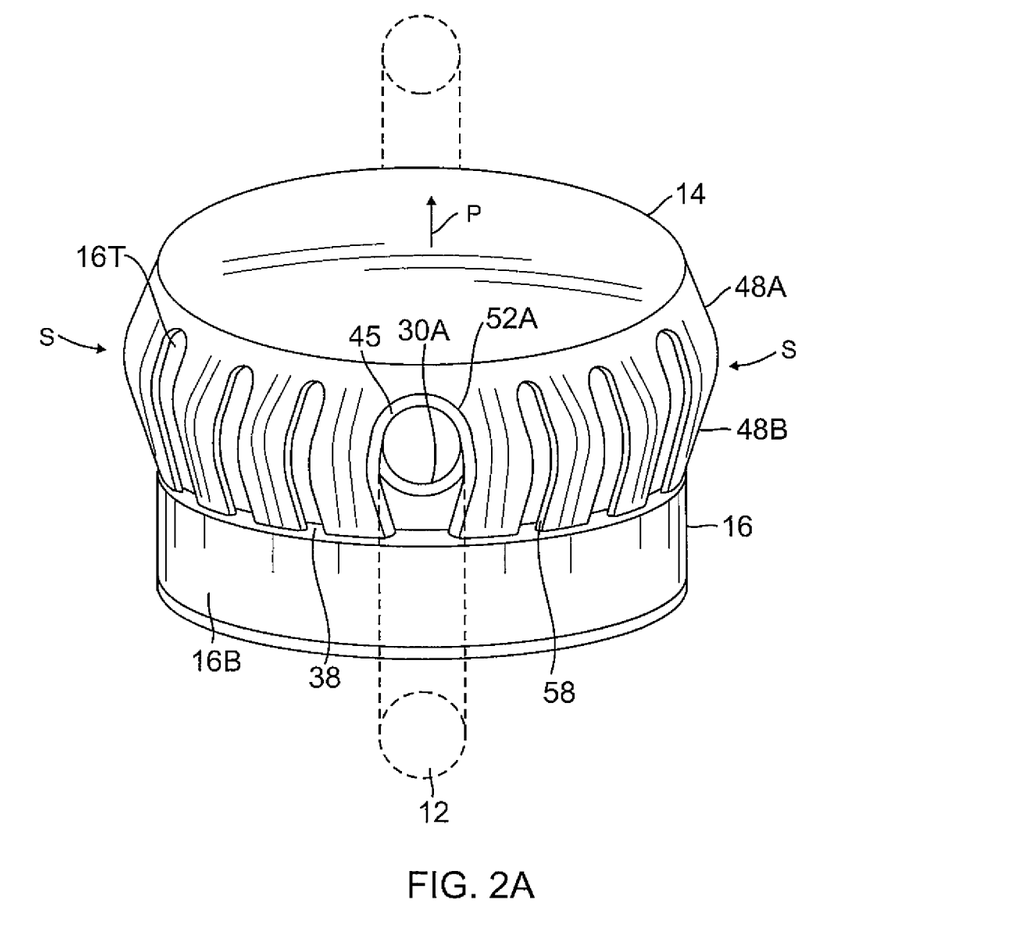
FIG. 2A is a perspective view of the device of FIG. 1 in a closed configuration.

As shown in FIG. 2A, when the lid 14 is engaged with the base 16, the device 10 is adapted to hold and restrain the tensile member 12 situated in the recessed formation 30. The skirt of the lid 14 has at least two clamping portions defined by inlet and outlet gaps 52A and 52B between adjacent finger members 48 and adapted to align with the ends 30A and 30B of the recessed formation 30 of the base 16 so that each inlet and outlet gap can straddle and clamp down on the tensile member 12 at at least two different locations to releasably secure the tensile member between the lid 14 and the base 16. Each inlet and outlet gap 52A and 52B is shaped and sized in accordance with the shape and size of the tensile member 12 so that it can clamp and firmly grip the tensile member when the lid 14 is engaged with the base 16 in the closed position. Each inlet and outlet gap may be lined with a layer 45 of compressible friction-inducing padding material for clamping without damaging the tensile member 12. The size and dimensions of the depth D (FIG. 1), of the recessed formation 30 and of the inlet and outlet gaps 52A and 52B are predetermined according to the cross-sectional size of the tensile member 12, but they may also adjusted by adding or removing the padding material 35 lining the recessed formation 30 and the padding material 45 lining the inlet and outlet gaps 52A and 52B.

In use, the tensile member 12 is positioned so that a portion of the tensile member 12 sits in the recessed formation 30, and a distal portion and a proximal portion of the tensile member 12 extend outside of the device 10. The recessed formation 30 may be accessed by the tensile member 12 by a user removing the lid 14 from the base 16 or inserting the tensile member 12 into one gap 52A and out the other gap 52B in the lid 14 as it sits on the base 16. Where the lid 14 is then placed on the base 16 over the tensile member 20, the lid 14 is aligned with the base 16 so that the gaps inlet and outlet 52A and 52B straddle the tensile member 12.

With reference to FIG. 2A, to close the device 10, the user places one of his hands over the lid 14 which is positioned over the base 16, with his palm on the main sheet portion 44, closes his fingers around the finger members 48 and squeezes to exert a compressive or radially-inward force S (see FIG. 2A) on the finger members 48 which pops the main sheet portion 44 into a convex configuration as shown by the arrow P. Accordingly, the force S urges the lid 14 toward its neutral configuration. Advantageously, the lid 14 with its bent finger members 48 provides the device with an ergonomic shape that is easy for the user to grab and manipulate single-handedly.

Figure 2B:
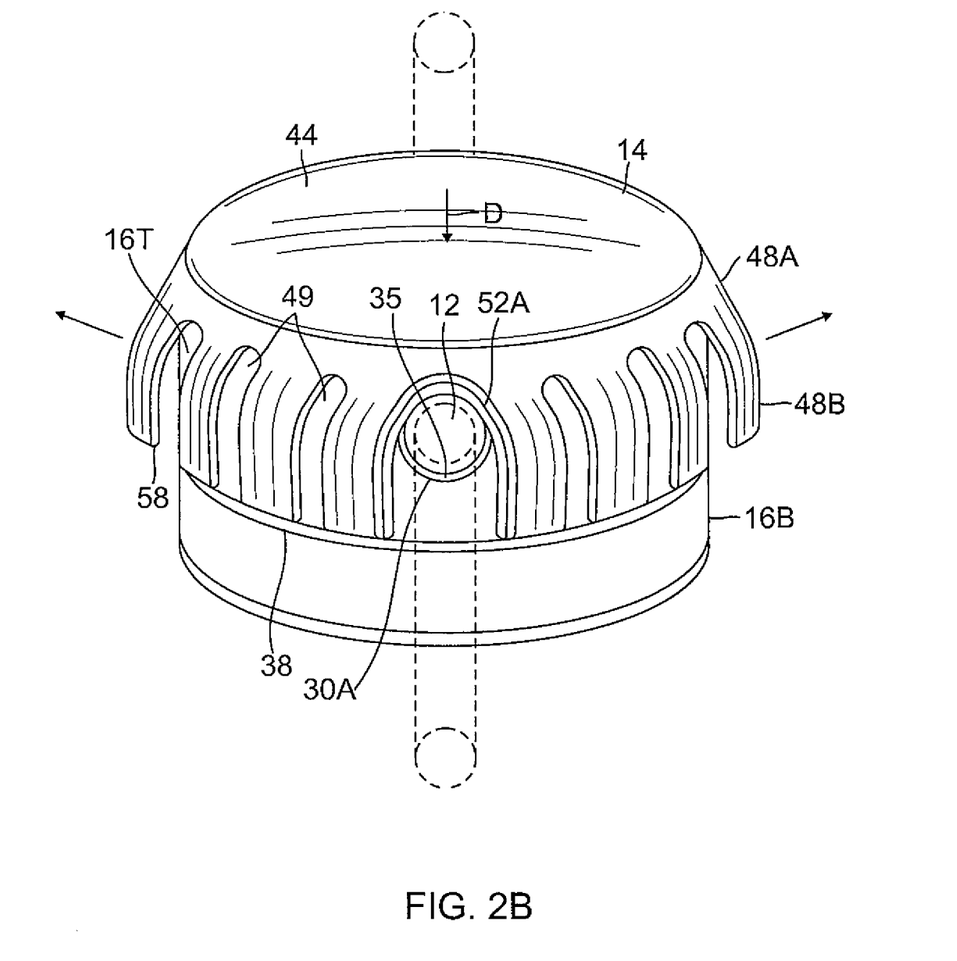
FIG. 2B is a perspective view of the device of FIG. 1 in an open configuration.
Figure 3B:
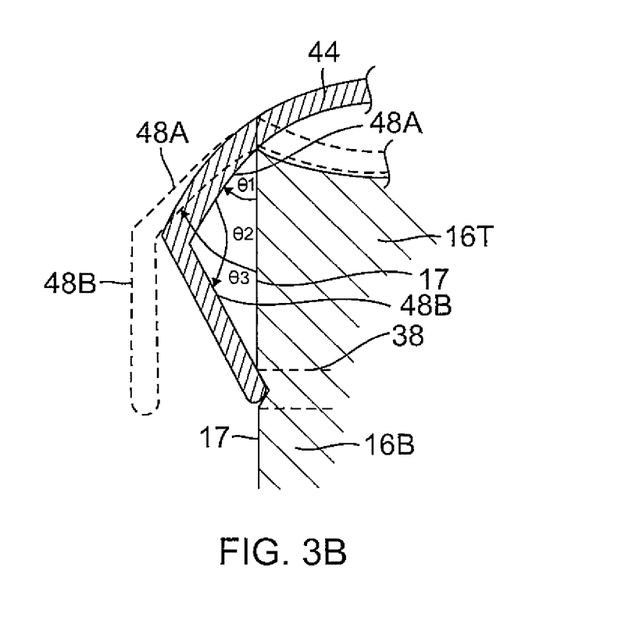
FIG. 3B is a detailed side cross-sectional view of a portion of a lid of the device of FIG. 3A.

With reference to FIGS. 2B and 3B, to release the lid 14 from the base 16 and allow adjustment or removal of the tensile member 12, the user applies a downward force D and depresses the main sheet portion 44 which flexes into a concave configuration that increases the angle at which the upper finger sections 48A extend from angle θ1 to θ3, where angle θ3 for the upper finger sections 48A ranges between about 55 and 75, preferably about 65. (The angle θ2 between the upper and lower finger sections 48A and 48B remains generally unchanged as the top main portion 44 of the lid flexes between its concave and convex shapes.) This movement disengages the lid 14 from the base 16 which releases the tensile member 12 from the grip of the inlet and outlet gaps 52A and 52B. By providing the top surface 22 of the base member 16 with a concave shape that corresponds and matches with the concave shape of a depressed main sheet portion 44 as shown in FIG. 3A, the top surface 22 acts as a stop prevent the user from using excessive force that may damage or permanently deform the lid 14.

By constructing the lid 14 out of a sheet material, the lid 14 can flex between the open and closed configuration under minimal force by the user. A depressive force D (FIG. 2B) by the user on the convex main sheet portion 44 flexes the main sheet portion into a concave shape which flexes the finger members 48 outwardly to release the lid 14 from the base 16. A slight compressive force S (FIG. 2A) by the user on the finger members 48 flexes the main sheet portion 44 into the convex shape which holds the finger members 48 inwardly to engage the base 16.

It is understood that the device can also be manufactured wherein the stamping permanently deforms the main sheet portion 44 conversely with the concavity shape and the finger members 48 with the angles of θ3 and θ2. So stamped, the lid 14 assumes this configuration in its relaxed or neutral state in which the distal ends of the finger members 48 trace a circumference 50 that is greater than the circumferential waist 38 of the base 16. It is understood that whether the neutral configuration is with the lid 14 expanded or contracted, closing the lid is accomplished by the user squeezing the finger members 48 and opening the lid is accomplished by the user depressing the main sheet portion 44.

Figure 5:
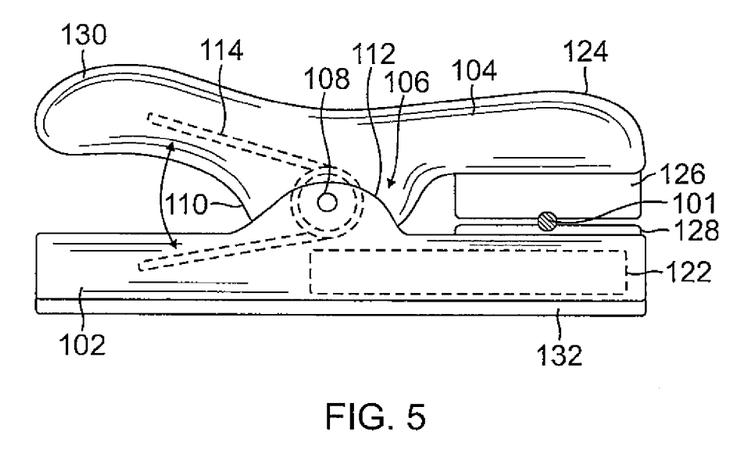
FIG. 5 is a side elevational view of a device of the present invention, according to another embodiment, in a closed configuration.
Figure 6:
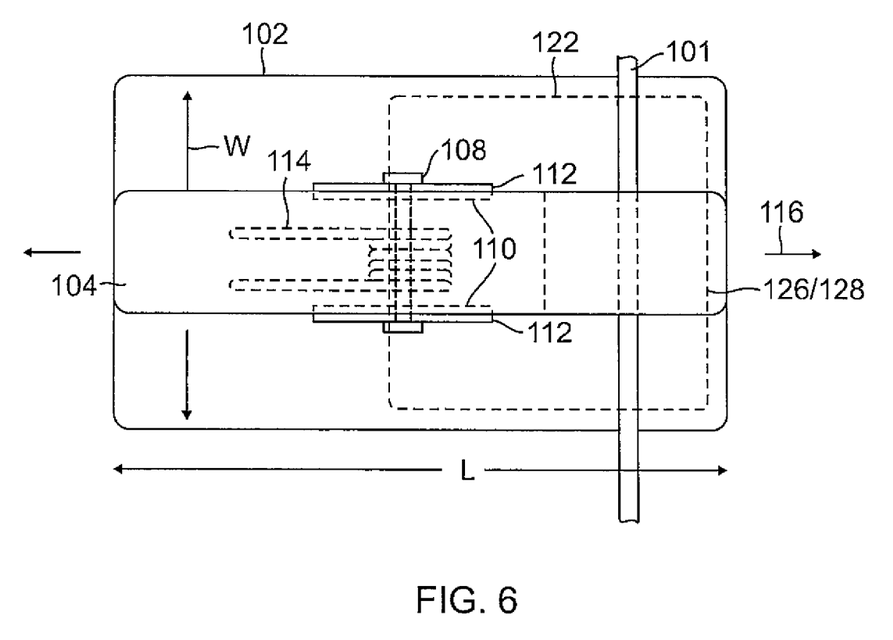
FIG. 6 is a top plan view of the device of FIG. 5.
Figure 7:
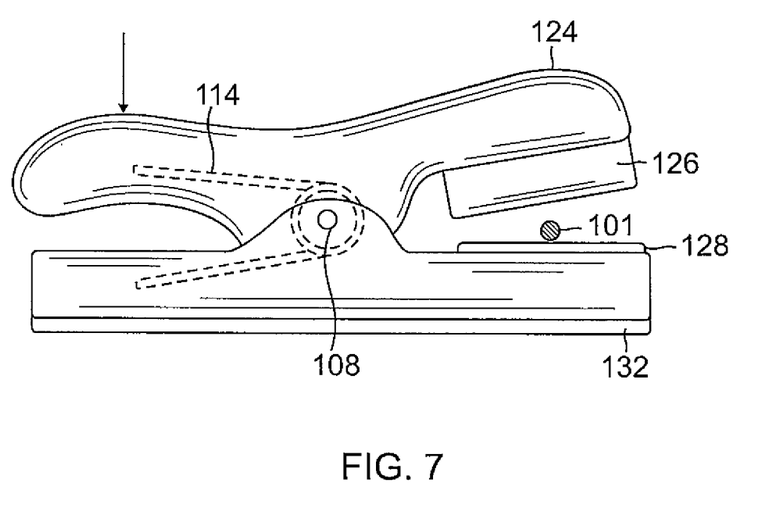
FIG. 7 is a side elevational view of the device of FIG. 5, in an open configuration.

FIGS. 5, 6 and 7 illustrate another embodiment of the present invention. A clamp device 100 for restraining a tensile member 101, including, for example, a guide wire, has a base member 102 and a top member 104 pivotable relative to the base member 102 via a pivot connection 106, e.g., a pin 108 that extends through pairs of overlapping fins 110 and 112 extending, respectively, from the top member 104 and the bottom member 102, that allows the device to move between a closed position restraining the guide wire 101 (FIG. 5) and an open position releasing the guide wire 101 (FIG. 7). A bias member, 114, e.g., a leaf spring around the pin, is provided to bias the device toward the closed position.

The base member 102 has a longitudinal axis 116 defining a length L and a width W, and an upper surface 118 and a lower surface 120. The base member has a mass that weighs down the device 100 for stability. In that regard, the base member 102 may be constructed of one or more weighty materials and/or it may have an inner cavity 122 (shown in broken lines) which is filled with a weighty material, such as sand or fluid. The top member 104 is elongated relative to the base member 102, having generally the same length but a lesser width. The top member 104 is aligned along the longitudinal axis 108 and the pivot connection 106 between the base and top members is generally located at a centered location thereof along the longitudinal axis. On one side of the pivot connection 106 is a securing end 124 of the top member 102 equipped with a pad 126 to contact and press on the guide wire 101 against the base member 102 to restrain the guide wire 101. The base member 102 may also have a pad 128 opposite of the pad 126. On the opposite side of the pivot connection 106 is a handle portion 130 of the top member 104 adapted for a user to depress single-handedly for raising the securing end 124 against the bias force of the bias member 114. The top member 104 therefore can be pivoted about the pivot connection 106 between the open position and the closed position. The top and base members 104 and 102 may be formed of any suitable material, including, for example, metal or plastic. The pads 126 and 128 may be formed of a friction-inducing material, for example, rubber.

At least a portion of the lower surface 112 of the base member, if not the surface in its entirety, is covered by a layer of friction-inducing material or adhesive 132 to secure the device on a support surface, for example, a patient's bed or body. Other fasteners that may be applied to the device and/or the lower surface 112 include suction cup(s), magnets, screws, ties, or the like.

The preceding description has been presented with reference to presently preferred embodiments of the invention. Workers skilled in the art and technology to which this invention pertains will appreciate that alterations and changes in the described structure may be practiced without meaningfully departing from the principal, spirit and scope of this invention. As understood by one of ordinary skill in the art, the drawings are not necessarily to scale. Also, different features may be combined within one or more embodiments as needed or appropriate. Moreover, the catheters described herein may be configured to apply various energy forms, including microwave, laser, RF and/or cryogens. Accordingly, the foregoing description should not be read as pertaining only to the precise structures described and illustrated in the accompanying drawings, but rather should be read consistent with and as support to the following claims which are to have their fullest and fair scope.

What is claimed is:

1. A device for restraining a guide wire, comprising:
   a base member having a top surface and a recessed channel across the top surface, the recessed channel being configured to receive a portion of the guide wire and to allow passage of the guide wire through the base member; and
   a flexible lid member configured to fit on the base member, the lid member having a main sheet portion covering the top surface of the base member and configured to cover the received portion of the guide wire extending through the recessed channel, the main sheet portion having a peripheral edge and a plurality of finger members separated by gaps, each of the gaps being disposed between adjacent finger members, the finger members extending downwardly from the peripheral edge at a first angle to surround an upper portion of the base member, the gaps including a first gap and a second gap, the first and second gaps configured to allow passage of the guide wire through the lid member, the lid member being flexibly movable between a closed configuration and an open configuration,
   wherein the lid member in the closed configuration is defined by the main sheet portion having a convex shape in which the plurality of finger members are flexed with a smaller first angle with the main sheet portion, and wherein the lid member in the open configuration is defined by the main sheet portion having a concave shape which flexes the plurality of finger members into a larger first angle with the main sheet portion.

2. The device of claim 1, wherein the gaps increase in size when the lid member is in the open configuration and the gaps decrease in size when the lid member is in the closed configuration.

3. The device of claim 1, wherein each finger member is bent at a junction between an upper portion and a lower portion of each finger member.

4. The device of claim 3, wherein a circumference traced by the junctions of the finger members is larger than a circumference traced by distal ends of the finger members when the lid member is in the closed configuration.

5. The device of claim 3, wherein a circumference traced by distal ends of the finger members is equal to or greater than a circumference traced by the junctions of the finger members when the lid member is in the open configuration.

6. The device of claim 1, wherein the base member has a circumferential groove that visually divides the base into the upper portion and a lower portion.

7. The device of claim 6, wherein a distal end of each finger member releasably engages the circumferential groove when the lid member is in the closed configuration.

8. The device of claim 7, wherein the plurality of finger members ranges between about ten and twenty.

9. The device of claim 6, wherein the circumferential groove has a circumference that generally equals a circumference traced by distal ends of the plurality of finger members when the lid member is in the closed configuration.

10. The device of claim 6, wherein the circumferential groove has a circumference that is smaller than a circumference traced by distal ends of the plurality of finger members when the lid member is in the open configuration.

11. The device of claim 1, wherein each of the first and second gaps is lined with a friction-inducing material.

12. A device for restraining a guide wire, comprising:
    a base member having a top surface and a recessed channel across the top surface, the recessed channel being configured to receive a portion of the guide wire extending through the recessed channel and to allow passage of the guide wire through the base member, the base member having a circumferential groove; and
    a flexible lid member configured to fit on the base member, the lid member having a main sheet portion covering the top surface of the base member and configured to cover the received portion of the guide wire, the main sheet portion having a peripheral edge and a plurality of finger members separated by gaps, each of the gaps being disposed between adjacent finger members, the finger members extending downwardly from the peripheral edge at a first angle to surround an upper portion of the base member, the gaps including a first gap and a second gap, the first and second gaps configured to allow passage of the guide wire through the lid member, the lid member being flexibly movable between a closed configuration and an open configuration,
    wherein the lid member in the closed configuration is defined by the main sheet portion having a convex shape in which the plurality of finger members are flexed inwardly such that distal ends of the finger members engage the circumferential groove, and wherein the lid member in the open configuration is defined by the main sheet portion having a concave shape which flexes the plurality of finger members outwardly such that the distal ends of the finger members release from the circumferential groove.

13. The device of claim 12, wherein the device is adapted to fit within a user's palm.

14. The device of claim 12, wherein the lid member is constructed of sheet metal material.

15. The device of claim 12, wherein the lid member is constructed of sheet plastic material.

* * * * *